(12) United States Patent
Von Stenglin (10) Patent No.: US 8,428,447 B2
(45) Date of Patent: Apr. 23, 2013

(54) FLASH VAPOR GENERATOR AND ASSEMBLY COMPRISING A FLASH VAPOR GENERATOR

(75) Inventor: Christoph Von Stenglin, Radolfzell (DE)

(73) Assignee: Metall + Plastic GmbH, Radolfazell (DE)

( * ) Notice: Subject to any disclaimer, the term of this patent is extended or adjusted under 35 U.S.C. 154(b) by 0 days.

(21) Appl. No.: 13/518,425

(22) PCT Filed: Dec. 22, 2010

(86) PCT No.: PCT/EP2010/007862
§ 371 (c)(1),
(2), (4) Date: Jun. 22, 2012

(87) PCT Pub. No.: WO2011/076400
PCT Pub. Date: Jun. 30, 2011

(65) Prior Publication Data
US 2012/0258023 A1    Oct. 11, 2012

(30) Foreign Application Priority Data
Dec. 23, 2009  (DE) .......................... 10 2009 060 512

(51) Int. Cl.
*A01G 13/06*   (2006.01)

(52) U.S. Cl.
USPC ............ 392/386; 392/394; 239/136; 422/307

(58) Field of Classification Search ................... 422/28, 422/307; 239/136; 392/386, 394, 399
See application file for complete search history.

(56) References Cited

U.S. PATENT DOCUMENTS

| 4,797,255 | A | 1/1989 | Hatanaka et al. |
| 6,339,678 | B1 | 1/2002 | Sorensen |
| 7,713,473 | B2 * | 5/2010 | Kendall et al. .................. 422/28 |
| 2007/0003431 | A1 | 1/2007 | Kendall et al. |
| 2008/0307825 | A1 | 12/2008 | Kolb et al. |

OTHER PUBLICATIONS

International Search Report, Apr. 5, 2011, for International Patent Application PCT/EP2010/007862 filed Dec. 22, 2010.

* cited by examiner

*Primary Examiner* — Sean E Conley
(74) *Attorney, Agent, or Firm* — Kacvinsky Daisak PLLC (57) ABSTRACT

A device is disclosed for generating a decontamination agent vapor, in particular hydrogen peroxide vapor. The device includes an evaporator body, a heating unit for heating the evaporator body, and a plurality of feed channels for feeding decontamination liquid to the evaporator body. The decontamination liquid is evaporated by the evaporator body. In one embodiment, the liquid contains hydrogen peroxide. In some embodiments, a plurality of blind holes are provided in a single- or multi-part evaporator body, and at least one of the feed channels is assigned to the blind holes.

19 Claims, 9 Drawing Sheets

FLASH VAPOR GENERATOR AND ASSEMBLY COMPRISING A FLASH VAPOR GENERATOR

BACKGROUND

The invention relates to a device for generating decontamination agent vapor, in more particularly to a device for generating hydrogen peroxide vapor using an evaporator body, a heating unit for heating the evaporator body and a plurality of feed channels for feeding decontamination liquid to be evaporated.

Hydrogen peroxide vapor is used for the decontamination of isolators and/or locks in the pharmaceutical industry, due to its high reactivity. Hydrogen peroxide vapor is obtained by evaporating an aqueous hydrogen peroxide solution. To minimise the explosion risk during the evaporation of solutions containing hydrogen peroxide, so-called flash evaporators (also known as flash vapor generators) are used, with the aim of the continuous, rapid (i.e., in a flash) evaporation of small quantities of liquid containing hydrogen peroxide. It is not permitted for larger quantities of liquid containing hydrogen peroxide to be boiled, due to the aforementioned explosion risk. The difficulty in evaporating small quantities of hydrogen peroxide-containing liquid, particularly aqueous solutions, is the formation of liquid droplets which "dance" on hot evaporator surfaces and impede efforts towards rapid evaporation.

A hydrogen peroxide vapor generator with a flat evaporator surface is known from DE 10 2006 006 095 A1. The aforementioned "dancing" droplet formation can take place with such a device.

An alternative flash evaporator (i.e., high-speed evaporator) is known from EP 0 972 159 B1, which is characterised by evaporator channels disposed in an evaporator body in a hydraulically interconnecting manner. The design is relatively complex. In relation to the further state of the art, reference is made to DE 602 03 603 T2 or DE 603 00 820 T2.

A hydrogen peroxide evaporator with a pot-like housing and an evaporator body is known from DE 2005 030 822 A1. This evaporator has a single, large-scale evaporator surface, and heat is supplied to the decontamination agent only from below. This evaporator is in need of improvement in terms of its evaporation rate and also in relation to the avoidance of "dancing" decontamination agent droplets. It is further known from DE 2005 030 822 A1 to use a plurality of evaporators each connected via one line to a vessel requiring sterilization, in order to increase the total amount of decontamination vapor. The total evaporator costs are therefore incurred x-times. In addition, a plurality of vapor lines must be conducted into the space to be evaporated, which is problematic in the case of small spaces due to lack of available space. In addition, a plurality of seals must then be provided.

A water evaporator is known from CN 2009 43844 Y. This evaporator has an evaporator body with a plurality of small holes. A single feed channel is jointly assigned to these holes, and the feed channel is disposed centrally above the evaporator body. So that the plurality of small holes can make their contribution to the evaporation, a sufficiently large quantity of liquid must be fed through the single feed channel, although this would runs counter to the goal of the spontaneous flash evaporation of decontamination agents. In practice, this would result in a hazardous boiling of decontamination agents. This evaporator is not therefore suitable for evaporating decontamination agents.

All the aforementioned flash evaporators are characterized by a comparatively complex design and/or by an evaporation rate capable of improvement.

SUMMARY

Based on the aforementioned state of the art, the problem addressed by the invention is that of indicating a flash evaporator (i.e., a high-speed evaporator) with the simplest possible design to generate decontamination agent vapor, and which is also characterized by a high evaporation rate. The formation of "dancing" decontamination agent liquid droplets within the evaporator should preferably be largely avoided. Moreover, an assembly is disclosed comprising a space to be decontaminated and a correspondingly improved vapor generator. This is preferably an assembly for decanting and/or processing pharmaceuticals.

In relation to the high-speed vapor generator, the problem is solved in the case of a generic device, in that a plurality of blind holes are provided in a one-part or a multi-part evaporator body and the blind holes are each assigned at least one, preferably exclusively one, feed channels in order to conduct the decontamination agent liquid to be evaporated, preferably in droplets. The decontamination liquid to be evaporated is preferably an aqueous solution of hydrogen peroxide, quite preferably a 35% to 50% solution.

In relation to the assembly, preferably a pharmaceutical assembly, the problem is solved through the use of a vapor generator designed as previously described. Thus, the invention relates to a device for generating decontamination agent vapor, and more particularly to a device for generating hydrogen peroxide vapor using an evaporator body, a heating unit for heating the evaporator body and a plurality of feed channels for feeding decontamination liquid to be evaporated. In some embodiments, the liquid contains hydrogen peroxide. The invention preferably relates to a so-called flash vapor generator (i.e., a high-speed vapor generator). The invention further relates to a preferably pharmaceutics-based assembly comprising a space to be decontaminated, particularly an isolator and/or a lock, and a device for generating decontamination agent vapor.

Advantageous developments of the invention are specified in the dependent claims. Included within the framework of the invention are all combinations of at least two features disclosed in the description, claims and/or figures. To avoid repetition, features disclosed with respect to the device should also be regarded as disclosed and claimable with respect to the method. Similarly, features disclosed with respect to the method should also be regarded as disclosed and claimable with respect to the device.

The invention is based on the knowledge that rapid evaporation of decontamination liquid fed preferably in droplets can be achieved in relation to the evaporation rate in an improved, simplified manner in that the evaporation takes place within peripherally closed blind holes in a one-part or multi-part evaporator body. This is due to, among other things, the fact that the heated peripheral wall of each of the blind holes is at a significantly smaller distance from the decontamination liquid fed for evaporation than a peripheral wall of a cylindrical evaporator with a level base area. In a high-speed evaporator designed according to the concept of the invention, a larger amount of heat can thereby be fed to the decontamination liquid to be evaporated, preferably fed in droplets, in the shortest possible time. Evaporation is not, therefore, caused merely from the application of heat from below, but also through radiation heat from the peripheral wall of the corresponding blind hole. Through the provision of blind holes in an evaporator body (particularly an evaporator block), which may be produced as bores for example, an exceptionally simple and effective evaporator device design is achieved. Unlike evaporators known from the state of the art, it is not necessary to provide evaporator channels crossing the evaporator body, through which the liquid to be evaporated is conducted, and where the aforementioned channels in the state of the art are also hydraulically interconnected in a costly manner. Quite particularly advantageous is an embodiment of the device for generating decontamination agent vapor in which a preferably one-part evaporator body is formed from aluminium, particularly an aluminium alloy, to achieve optimum heat conduction. It is still further preferred for the heating unit to be designed and set such that it heats the evaporator body to a temperature within a temperature range of between about 100° C. and about 140° C. It is quite particularly preferable for the temperature to be around 120° C. or less during evaporator operation, so that the formation of closed, not suddenly evaporating, droplets on the evaporator surface is optimally prevented. In some embodiments the maximum diameter of the blind holes—preferably with cylindrical contours at least in section—does not exceed a dimension of 50 millimeters (mm). In other embodiments the maximum diameter to be 40 mm or under. In still further embodiments the diameter is selected from a range of values of between roughly 30 mm and 35 mm. Ideally, the maximum depth extension of the blind holes (i.e., holes closed at the bottom) is also limited and amounts to under 50 mm, preferably under 40 mm, even more preferably under 30 mm. The depth extension as far as the base of the blind hole is preferably about 25 mm.

In one embodiment the blind holes do not have a circular cross-sectional shape, but rather have a rectangular cross-sectional shape which, in some embodiments is at least approximately square. In other embodiments, the blind holes have no sharp edges, but rather have edges exhibiting a radius such that they are rounded. Although this embodiment seems unusual, since blind holes with rectangular contours are comparatively expensive to produce compared with blind holes with circular contours, particularly due to the milling, surprisingly optimized evaporation properties can be achieved using the rectangular cross-section (i.e., with two pairs of parallel sides disposed at right angles), preferably with rounded corners.

It is particularly advantageous for the length to width ratio of the blind holes to be about 1 to about 1.3, particularly preferably about 1.1. In a quite particularly preferred embodiment, the length of each blind hole (measured towards the longitudinal extension of the evaporator) is about 27.75 mm and (the width extending perpendicularly thereto) is about 25 mm. Particularly preferably, the depth of the blind holes with a rectangular contour is roughly 24 mm. Thus, the ratio between the length, width and depth is approximately 1:1:1. It has proved particularly advantageous for blind holes with a rectangular contour to be disposed in a row. In one embodiment, six identical blind holes are disposed in a row (i.e. behind one another in the longitudinal extension of the evaporator), where two adjacent blind holes in each case are spaced from one another by fewer than 10 mm, and preferably by about 4 mm.

The number of blind holes provided and/or to be supplied with decontamination liquid may be adjusted so as to adjust an active agent concentration in the carrier air and/or in the atmosphere of the space to be decontaminated. In accordance with the invention, at least one, and preferably only one, feed channel is allocated to each of the blind holes for feeding of decontamination agents to be evaporated. In some embodiments the decontamination agents are fed in droplets, which means that the feed channels are disposed such that the decontamination agent to be evaporated can be fed directly into the blind holes, preferably by dropping the agent into the holes.

There are a variety of different possibilities with regard to the geometric design of the blind holes. In one embodiment they have a cylindrical casing surface, preferably coupled with a circular base surface. Alternatively, the blind holes may have a cylindrical casing surface coupled with a conical base section.

As previously explained, the blind holes may have a rectangular cross-section, and in some cases they exhibit an approximately square contour. It may also be preferable for the hole edges (i.e., the edges running in an upright direction when viewed in the peripheral direction) to be rounded. For example, in some embodiments the edges have a curvature radius of roughly R=5 mm.

In accordance with an alternative embodiment, the diameter of the cross-sectional surface of the blind holes, which may have a circular contour, diminishes as the distance from their upper inlet opening increases. Alternatively the blind holes may have a stepped reduction in cross-section, or they may be reduced in a continuous fashion so as to have a conical shape when viewed in cross-section.

In some preferred embodiments, all blind holes have an identical shape.

In a further development of the invention, it is advantageously provided that the blind holes are not immediately adjacent to one another, but are spaced apart from one another, so as to guarantee a uniform heat supply. The blind holes also are preferably not hydraulically interconnected directly, such as by cross-bores.

There are also different possibilities with regard to the specific embodiment of the evaporator body. Evaporator bodies known in the art usually have a cylindrical contour. In one embodiment of the presently disclosed evaporator body, the body has a greater length dimension than the width dimension, and preferably also a greater length dimension than the depth dimension is preferred. It is quite particularly advantageous for the evaporator body to have at least an approximately square contour at least in section.

There are also different possibilities with regard to the arrangement of the blind holes. In one embodiment, at least one, preferably one one, row of blind holes extending in the direction of the longitudinal dimension of the evaporator body is provided. An embodiment with a plurality of particularly parallel rows can also be achieved.

The heating unit is preferably designed and disposed in such a manner that it extends along the longitudinal sides, i.e. along the longitudinal dimension of the evaporator body. It preferably also extends, in addition, along the base surface. In some embodiments, two, particularly parallel, rows of blind holes are provided, if the heating unit extends into an area between the rows, so that a uniform supply of heat to the blind holes can thereby be guaranteed. The heating unit is preferably an electrical resistance heater. A temperature sensor, for example a PT 100, is advantageously included in the evaporator body. The temperature sensor, particularly the PT 100, may be used to monitor and record the temperature and the temperature course. In addition to, or as an alternative to, the temperature sensor, a thermocouple for the heating device is provided. The heating unit may be at least a heating rod, which is preferably contained in an opening, particularly a bore, running in the direction of the evaporator's longitudinal dimension. The thermocouple may be disposed in this opening, preferably integrally with the heating rod. In other embodiments, a plurality of heating rods, particularly disposed in parallel, are provided. Good results have been obtained with a total of three heating rods, where the three heating rods are controlled by means of a joint thermocouple. The thermocouple may be located in a central bore or opening along with the central heating rod. In one embodiment, only two heating rods are disposed symmetrically relative to a perpendicular mirror plane.

To prevent the decontamination liquid conducted through the feed channels from being entrained by carrier air before the liquid is evaporated, the feed channels may penetrate the inlet openings of the blind holes so as to project into the blind holes. It is preferred that dry and heated carrier air flows over the blind holes and thereby entrains the decontamination agent vapor rising from the blind holes.

In practice, the feed channels may become encrusted or may be subject to wear. To avoid major repair work, the feed channels may be replaceable (i.e. configured in an interchangeable manner). Surprisingly, for the formation of the feed channels, injection needles available in bulk and particularly made of stainless steel can be used for this application. Such needles may be provided with a Luer-Lock connection fitting at their upper ends (i.e., the end opposite the blind holes), to facilitate this replaceability and interchangeability.

In some embodiments, the internal diameter of the feed channels is selected from a range of between about 0.5 mm and about 2 mm.

The feed channels, if they comprise injection needles, may be disposed in such a way that they supply decontamination liquid to be evaporated to the blind holes from a distributor chamber. As such, they represent the hydraulic connection between the distributor chamber and the blind hole in each case. For this purpose, the feed channels may project into a flow channel for carrier air disposed above the blind holes and therefore above the evaporator body or else they are disposed in said flow channel or preferably penetrate it up to and into the blind holes, in order to prevent an entrainment of as yet unevaporated decontamination liquid with the carrier air, as already described.

In one embodiment, the decontamination liquid can flow to the feed channels via a supply channel. Ideally, these supply channels are not flexible lines, but channels introduced into, specifically milled into, a metallic evaporator component. The supply channels may be provided in a cover plate and may connect a central supply line to the feed channels. In order to guarantee that the feed channels are each supplied with the same quantity of decontamination agent to be evaporated, the channels—based on an equal flow cross-section—may all be of the same length so that the liquid to be evaporated encounters the same flow resistance. The aforementioned supply channels may be supplied via a clocked metering pump disposed outside the actual evaporator. The supply channels may emerge from one, preferably central, space, which may be introduced as a recess in the cover plate with the supply channels. The supply channels may be sealed by a joint closing plate, for example, which can be secured to the cover plate by screws. In addition or alternatively, the supply channels may be sealed on their upper side by metal plates, particularly stainless steel plates, wherein the plates may be welded to the cover plate having the supply channels.

It is particularly advantageous if the flow volume of decontamination liquid can be set for the individual feed channels. In other words, it is preferable for at least some of the feed channels to be provided with a setting mechanism with which the flow volume for the particular feed channel can be set. These setting mechanisms are preferably located within, or close to, the previously described distributor chamber, into which decontamination liquid can be pumped from a store, which in one embodiment is an interchangeable storage bottle.

The invention also relates to an assembly, particularly a pharmaceutical assembly, comprising a space to be decontaminated with decontamination agent vapor, particularly an isolator and/or a lock, and also a device designed as described earlier for generating decontamination agent vapor, particularly hydrogen peroxide vapor.

In the state of the art, high-speed evaporators are customarily disposed in such a manner that they are supplied with air from the space being decontaminated as carrier air, and the carrier air is enriched with hydrogen peroxide and released straight back into the space to be decontaminated. This usually leads to condensation of hydrogen peroxide in the space being decontaminated. Condensation of this kind should be prevented wherever possible with the disclosed embodiments, since disclosed high-speed evaporator is not, or is not exclusively, supplied with carrier air from the space to be decontaminated, but rather is supplied with fresh air. Fresh air does not only mean preferably dry ambient air (particularly <10% relative atmospheric humidity), but also compressed air from corresponding storage vessels, particularly pressure cylinders. It is essential that this is not air fed from the space to be decontaminated. This requires air also to be continuously delivered from the space to be decontaminated into the environment, for example, in order to prevent impermissible overpressures. The advantage of an assembly of this kind is the improved controllability of the hydrogen peroxide concentration in the ambient air of the space to be decontaminated, as well as better pressure control during decontamination. The pressure in the space should be above ambient pressure during decontamination, preferably around 30 Pa above ambient. In relation to the specific configuration of the evaporator, there are two different possibilities. The evaporator may, for example, be connected to the single fresh air supply line (i.e., the carrier air supply line), so that all the air to be fed into the space to be decontaminated flows straight through the evaporator. It is preferable for the evaporator to be arranged in this way if the fresh air supply does not exceed 80 $m^3$ per hour during operation of the space to be decontaminated. In an alternative assembly, a bypass line is allocated to the single fresh air line (i.e., the supply line) which is disposed in the flow direction upstream of the evaporator, the evaporator being connected to the bypass line. This results in part of the fresh air supplied not passing directly through the evaporator, but instead being mixed with the diverted enriched carrier air passing through the evaporator before it reaches the space to be decontaminated. An assembly of this kind is particularly appropriate when the space to be decontaminated is in operation, i.e. following decontamination of a fresh air supply of over 80 $m^3$ per hour.

To set or control the decontamination agent vapor concentration in the carrier air, a regulation line may be used to discharge into an intermediate or connection line downstream of the evaporator, through which an adjustable volume of air, particularly of fresh air, can be mixed to dilute the vapor concentration in the carrier air.

Further advantages, features and details of the invention emerge from the following description of preferred embodiments and also from the drawings.

BRIEF DESCRIPTION OF THE DRAWINGS

FIG. 1 is a perspective view of an exemplary device for generating decontamination agent vapor, such as a high-speed evaporator or a flash evaporator,

FIGS. 2-5 are cross-section views of the device of FIG. 1.

DETAILED DESCRIPTION

Identical elements and elements with the same function are labeled in the figures using the same reference numbers.

Figure 1:
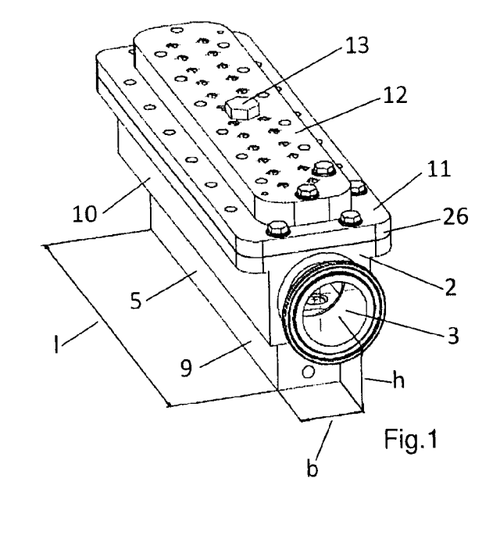

FIG. 1 shows a first exemplary embodiment of a device 1, such as a high-speed evaporator or flash evaporator, for generating decontamination agent vapor. In some embodiments the decontamination agent vapor is hydrogen peroxide vapor. In some embodiments the decontamination agent vapor is used to decontaminate a pharmaceutical packing device for drugs (not shown) disposed in an isolator.

The device 1 comprises a connector 3 for carrier air at a first end 2 for transporting away the decontamination agent vapor generated in the device, and directing it to a space to be decontaminated (not shown). At the second end 4 (FIG. 2) disposed opposite the first end 2, a connection is provided for coupling a connection line leading to the space to be decontaminated. The connections (disposed at ends 2 and 4) can be screwed into a lower device section 5 or into holes with an internal thread 6, 7 disposed therein.

A free cross-section (i.e. a flow channel 8), is disposed axially between the connections, through which the carrier air flows and can thereby take the decontamination agent vapor with it. The carrier air may be fresh air, which may be compressed air or ambient air.

The lower device section 5 comprises a metallic evaporator body 9, which in one embodiment is made of an aluminium alloy. As emerges from FIG. 1, the width extension "b" of said lower device section is significantly smaller than its length extension "1." The width extension "b" roughly corresponds to the height extension "h." As can be further seen from the figures, the evaporator body 9 is prismatic in form and is formed integrally with the metallic casing 10 that forms the flow channel 8 therein. An upper device section 11 is screwed to the lower device section 5 in a cover-type manner, which can be closed using a transport screw 13. The upper device section 11 comprises a distributor chamber 12 in which decontamination liquid to be evaporated can be supplied. In some embodiments, the decontamination liquid is an aqueous, preferably 35% hydrogen peroxide solution.

Figure 4:
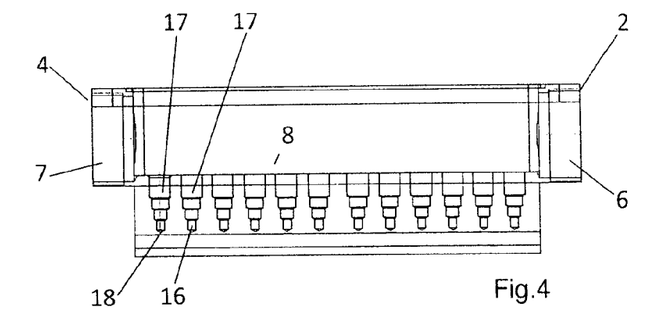

In the illustrated embodiment, two rows 14, 15 of blind holes 16 (i.e., holes only open at one end), are provided in the evaporator body 9. The holes are separate and are spaced apart from one another. The blind holes 16 and recesses are separate from one another in that they are not directly hydraulically interconnected. The blind holes 16 extend perpendicular to the carrier air flow direction, and thus they also perpendicular to the solution extension of the evaporator body 9. As can be seen in FIG. 4, the cross-sectional surface of the blind holes 16 diminishes, running from an inlet opening 17 to a blind hole base 18. In the exemplary embodiment shown, the blind holes 16 are multi-stage stepped bores. In an alternative embodiment, the blind holes can have a conical contour. As will be explained later with reference to FIG. 5, the flow channel 8 is crossed by needle-like feed channels running perpendicular to its longitudinal extension, through which decontamination liquid to be evaporated from the distributor chamber 12 is conducted in droplets to the individual blind holes 16. In this case, the feed channels arranged so as to be interchangeable across the inlet openings 17 so that the carrier air flowing through the flow channel 8 cannot entrain them.

Figure 3:
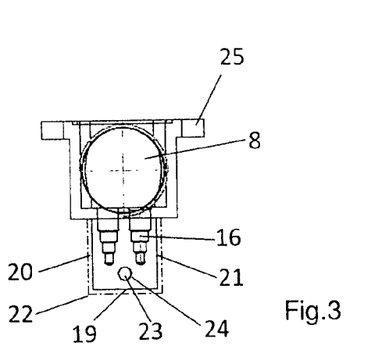

As shown in FIG. 3, the evaporator body 9 is surrounded at its base end 19 and also on both longitudinal sides 20, 21 by a heating unit 22, which in the illustrated embodiment is an electrical heating unit. The heating unit 22 is positioned adjacent to the evaporator body 9, and is controllable such that the evaporator body reaches a temperature of roughly 110° C. in the exemplary embodiment shown. The actual temperature can be measured using a temperature sensor 23, which can be inserted in a bore 24 extending in the direction of the longitudinal extension of the evaporator body 9.

Figure 2:
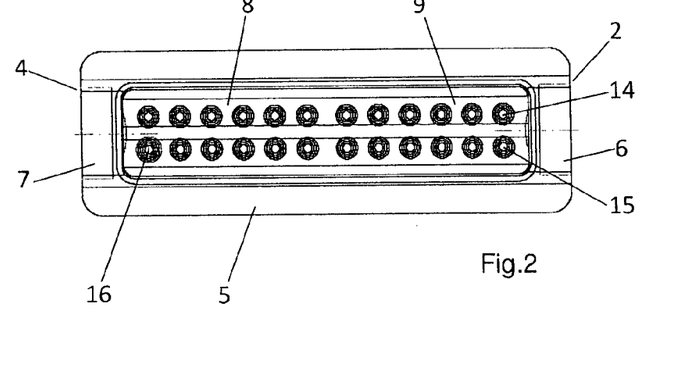

As shown in FIGS. 1-3, the lower evaporator section 5 includes a peripheral securing flange 25 at its upper end. The peripheral securing flange 25 engages a corresponding counter-flange 26 of the upper device section 11, and the two may be screwed together.

Figure 5:
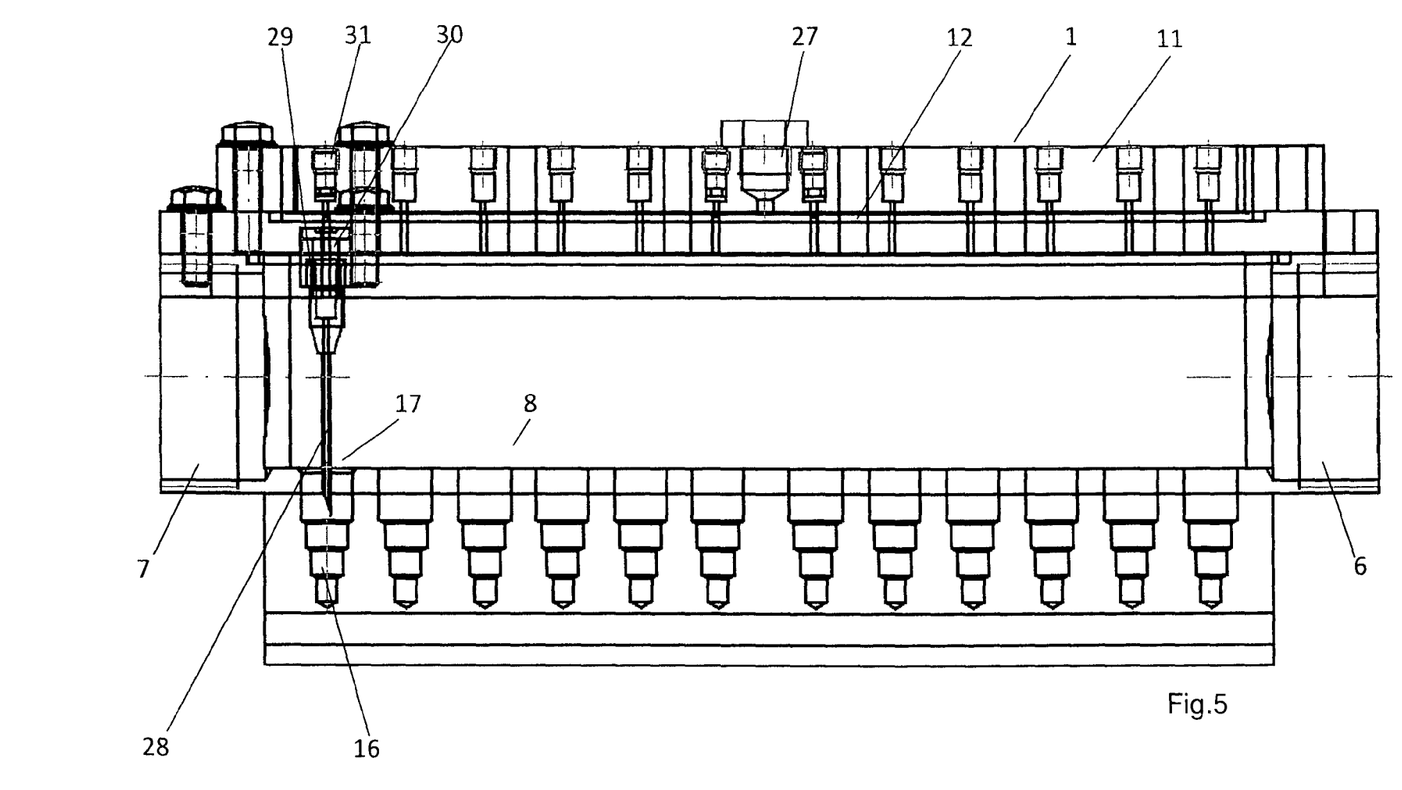
Figure 6:
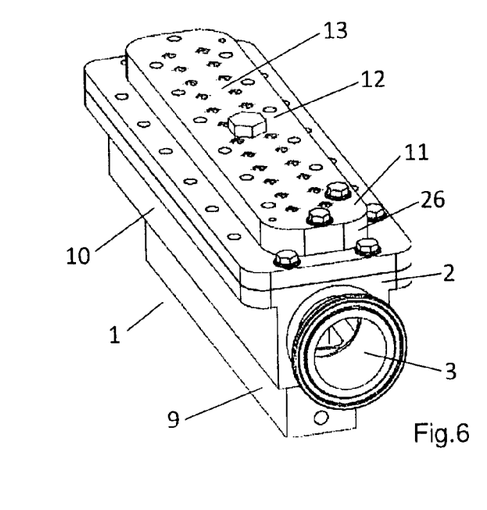
FIG. 6 is a perspective view of an exemplary alternative evaporator.
Figure 7:
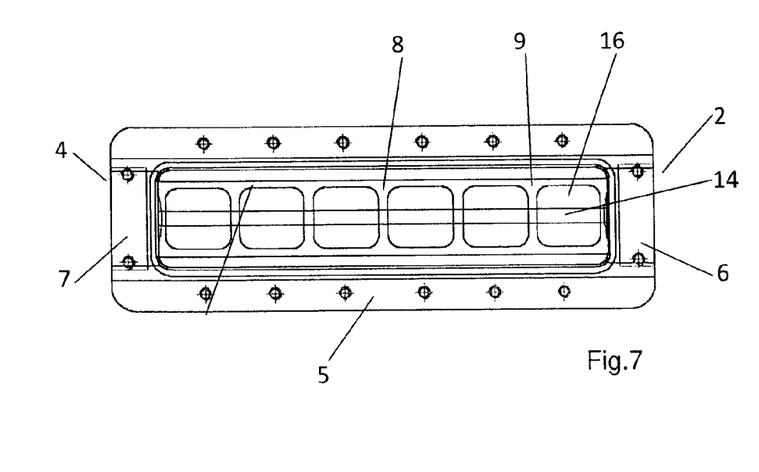
FIGS. 7-10 are cross-section views of the exemplary alternative evaporator of FIG. 6.
Figures 8, 9:
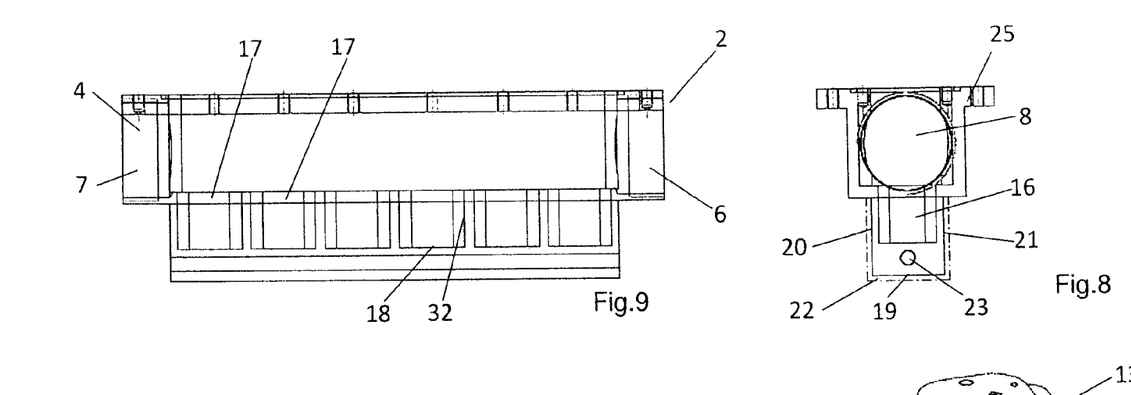
Figure 10:
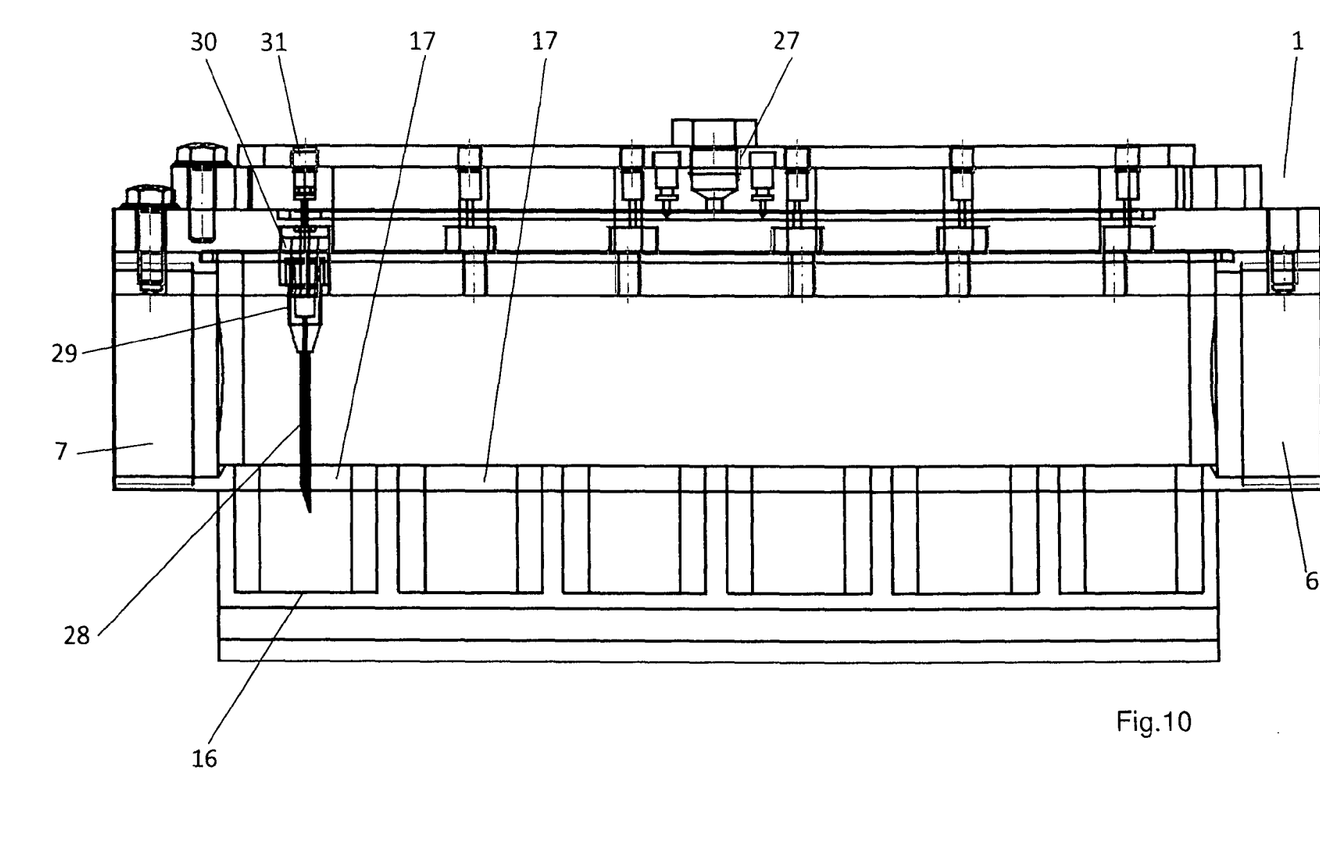

FIG. 5 illustrates a longitudinal section view of the mounted device 1. An upper central connection 27 is shown for coupling to a feed line for feeding decontamination liquid to be evaporated into the flat distributor chamber 12. To create the distributor chamber 12, the upper device section 11 and the housing walls thereof have a two-piece design.

As further shown in FIG. 5, each blind hole 16 is associated with a single feed channel 28, configured and disposed in an interchangeable manner. In the illustrated embodiment, the feed channels 28 comprise stainless steel injection needles. The injection needles include a Luer-Lock connection piece 29 on their upper sections, so that they can each be fixed to a corresponding adapter 30 on the upper device section 11 beneath the distributor chamber 12. For reasons of clarity, only a single feed channel 28 an associated adapter 30 is represented. It will be appreciated, however, that in practical application an adapter 30 of this kind with an associated feed channel 28 is allocated to each blind hole 16. As clearly shown, the feed channel 28 crosses the flow channel 8 perpendicular to it longitudinal extension, and enters the blind hole 16 beneath the inlet opening 17. A setting screw 31 is assigned to each feed channel 28, with which the volume of liquid flowing through the feed channel 28 and into the respective blind hole 16 can be set.

An alternative embodiment of the device 1 will now be described in relation to FIGS. 6-10. It will be appreciated that the device 1 of FIGS. 6-10 is generally similar to the embodiment of the device 1 shown in FIGS. 1-5 as previously described. To avoid repetition, only the differences between embodiments will be described. With regard to similarities, reference is made to FIG. 1 with the associated figure description.

In contrast to the embodiment described in relation to FIG. 1, the evaporator body 9 of the device 1 in accordance with FIGS. 6-10 comprises only a single row 14 of blind holes 16. In addition, the blind holes 16 of this embodiment do not have a conical or a stepped shape, but rather have a cylindrical shaped defined by cylindrical casing surface 32. In addition, the blind hole base 18 is preferably circular in form, as illustrated, to simplify manufacture. It will be appreciated, however, that it is also contemplated that a conical blind hold base could be used. In the exemplary illustrated embodiment, a total of six blind holes are provided. In a preferred embodiment, only five blind holes may be used. In other embodiments, a single feed channel 28, preferably formed by an injection needle, may be allocated to each blind hole 16.

In the interests of clarity, FIG. 10 again shows only a single feed channel 28, assigned to feed channel 28. The feed channel 28 has a Luer-Lock connection piece disposed at one end, which is interchangeably held in an associated adapter 30. As with the previous embodiments, it will be appreciated that in practical application each blind hole 16 will have its own feed channel 28, and that each feed channel 28 will be coupleable to an associated adapter 30.

Figure 11:
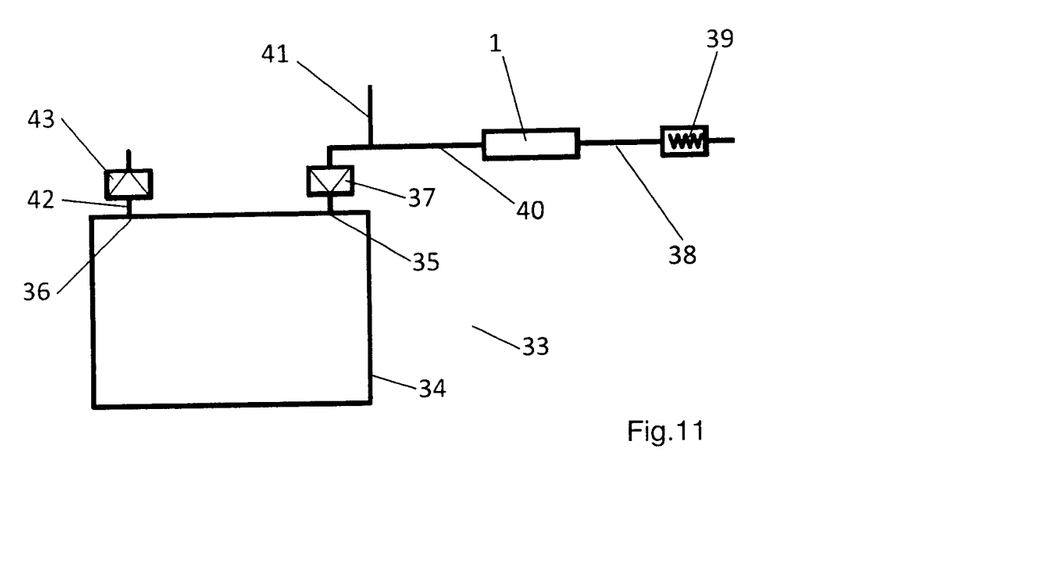
FIG. 11 is a schematic diagram of a pharmaceutical assembly comprising an isolator and a high-speed evaporator, and a single fresh air supply line connected directly to the evaporator.

FIG. 11 shows an arrangement 33, in this case a pharmaceutical arrangement, comprising a space 34 to be decontaminated having an inlet connection 35 and an outlet connection 36. In one exemplary embodiment, the space 34 is in the form of an isolator. A filter 37, which in one embodiment is a high efficiency particulate air (HEPA) filter, is associated with the inlet connection 35 so as to filter the incoming carrier air enriched with decontamination agent vapor. In an alternative embodiment, decontamination agent vapor can be fed directly into the space, and not through a filter. A device 1, which may be the device described in relation to the previous figures, and which in one embodiment is a high-speed evaporator, is connected directly to the single fresh air line 38 disposed upstream of the device 1 in the flow direction. Thus arranged, the total air flowing in through the fresh air line 38 flows through the device 1 and is thereby enriched with decontamination agent vapor. The carrier air, which may be fresh air, can be preheated by means of a temperature-regulating mechanism 39. The fresh air may come from a bottle of compressed gas, for example, or it may be drawn in from the environment. If drawn from the environment, an air drying mechanism is preferably provided. In the flow direction downstream of the device 1, a regulating line 41 discharges into line 40 (which may be termed an intermediate line) to enable controlled feed of additional fresh air so as to adjust the decontamination vapor concentration in the carrier air to be fed to the space 34. A discharge line 42 is connected to the outlet connection 36 though which the waste air can flow into the environment or to a catalytic converter in order for the hydrogen peroxide vapor to be broken down. In some embodiments, a filter 43 such as a HEPA filter, may be provided in the discharge line.

Figure 12:
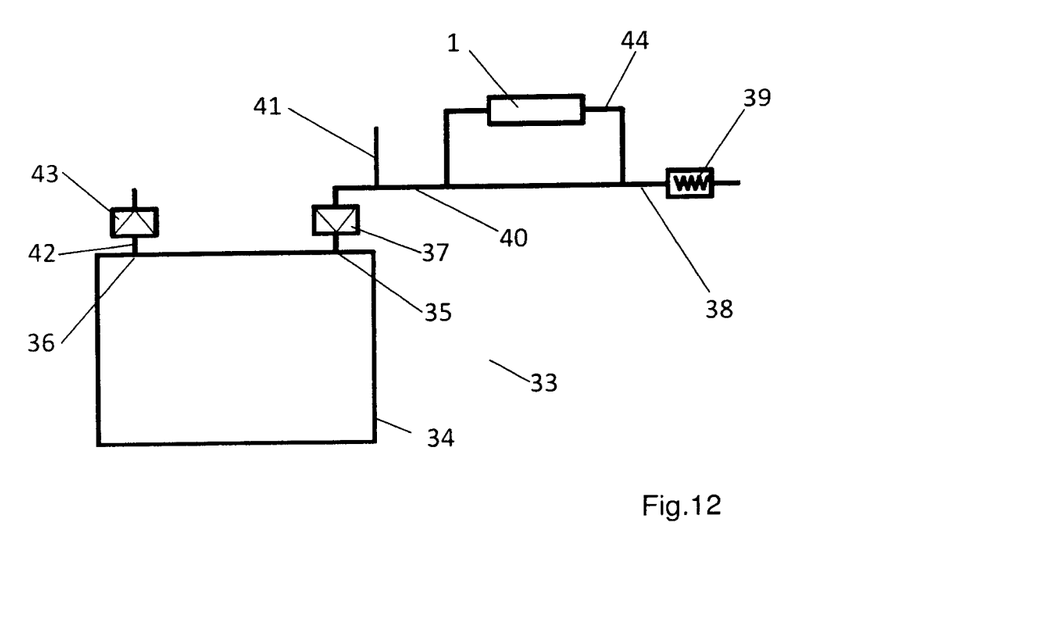
FIG. 12 is a schematic diagram of an alternative pharmaceutical assembly in which the evaporator is disposed in a bypass line of a fresh air supply line.

The assembly 33 of FIG. 12 is generally similar to the assembly of FIG. 11. To avoid repetition, only the differences between embodiments will be described. With regard to similarities, reference is made to FIG. 11 with the associated figure description.

It is evident that the device 1, which in the illustrated embodiment is a high-speed evaporator, is connected to a bypass line 44 to conduct fresh air 38, so that not all fresh air supplied flows through the device 1. As in the FIG. 11 embodiment, the decontamination principle is based on so-called fresh air decontamination—which means that only air not originating in the space 34 to be decontaminated, i.e. enriched with hydrogen peroxide vapor, is fed to the device 1. Such fresh air may be compressed air or particularly dried ambient air.

Figure 13:
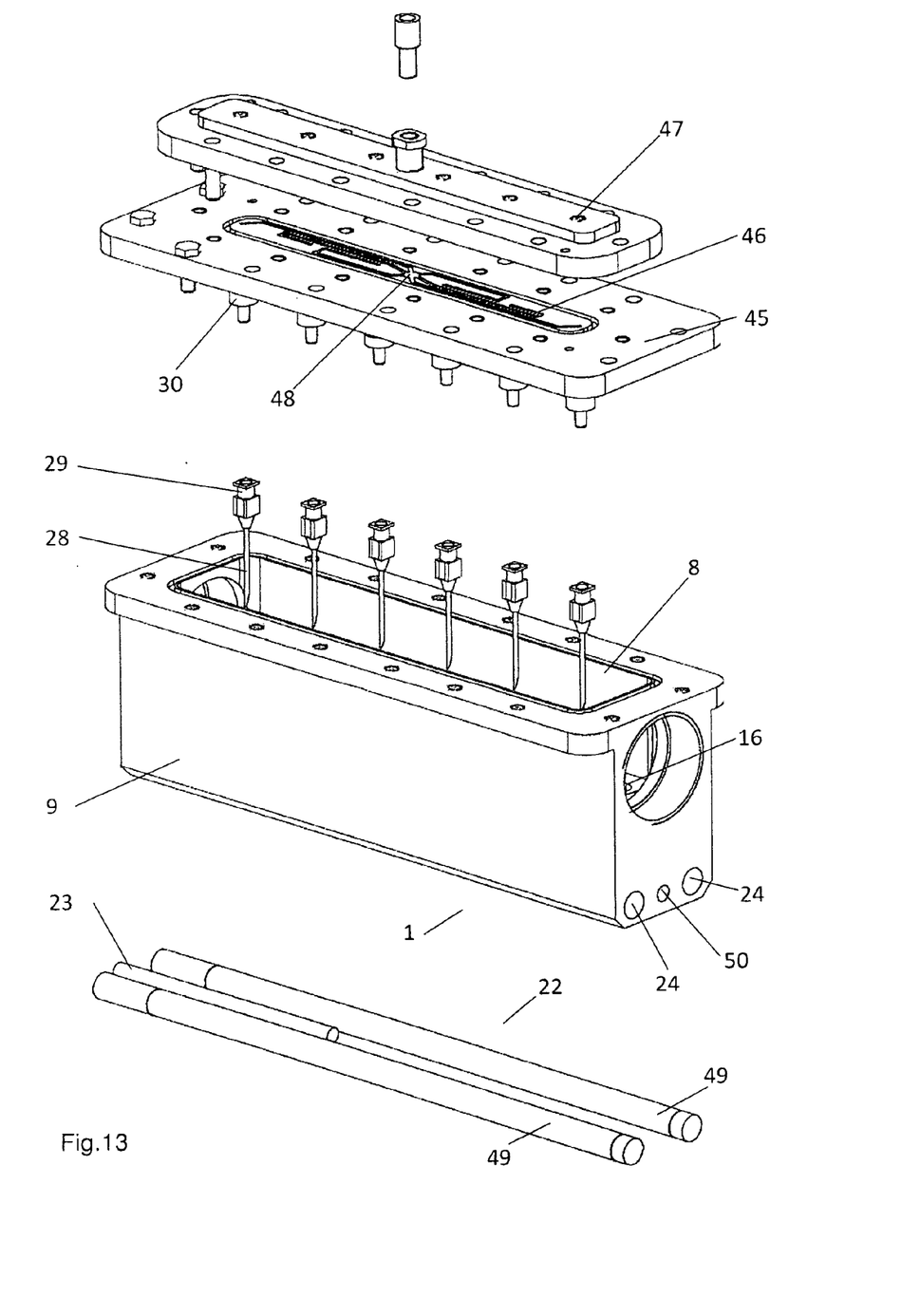
FIG. 13 is an exploded view of a further alternative embodiment of an evaporator.

FIG. 13 shows an alternative exemplary embodiment of a device 1, which may be a high-speed evaporator, or a flash evaporator, for generating decontamination agent vapor for decontaminating a pharmaceutical isolator. In one embodiment, the decontamination agent vapor is hydrogen peroxide vapor.

The device 1 comprises an evaporator body 9 having a trough-like form in an upper section and a prismatic form in a lower section, where the upper section laterally encloses a flow channel 8. A cover plate 45, which seals the top of the flow channel 8 in the mounted state, may be fastened to the evaporator body 9 by screws. Supply channels 46, which will be described in greater detail later, are provided in the cover plate 45 such as by milling. The supply channels 46 transport decontamination liquid to be evaporated to adapters 30 and interchangeable supply channels 28. The supply channels can take the form of injection needles made of stainless steel and can each have a Luer-Lock connection 29 at their upper end for fixing to associated individual adapters 30.

In the illustrated exemplary embodiment, the sealing plate 47, which can be screwed to the cover plate 16, closes the groove-like supply channels 46 from above. In addition or alternatively, the supply channels 46 may be closed with an upper wall, which may be welded on subsequent to assembly. The upper wall, in some embodiments, may be made of stainless steel.

The supply channels 46 can emerge from a central recess 48 into which decontamination liquid to be evaporated is fed by means of a clocked metering pump (not shown) via a supply line.

As can be further seen from FIG. 13, three parallel bores 24 extending in the direction of the longitudinal extension of the evaporator body 9 are provided in the evaporator body 9 in an area beneath blind holes 16. A heating rod 49 may be inserted in each bore 24. The heating rods 49 create the heating unit 22. Casing (i.e., jacket) heating is thus dispensed with in this embodiment. The center heating rod 49 is preferably assigned a thermocouple (not shown), with which the temperature of the three heating rods 49 can be controlled. In addition, a temperature sensor 23 can be inserted into an opening 50 positioned between bores 24.

Figures 14A, 14B:
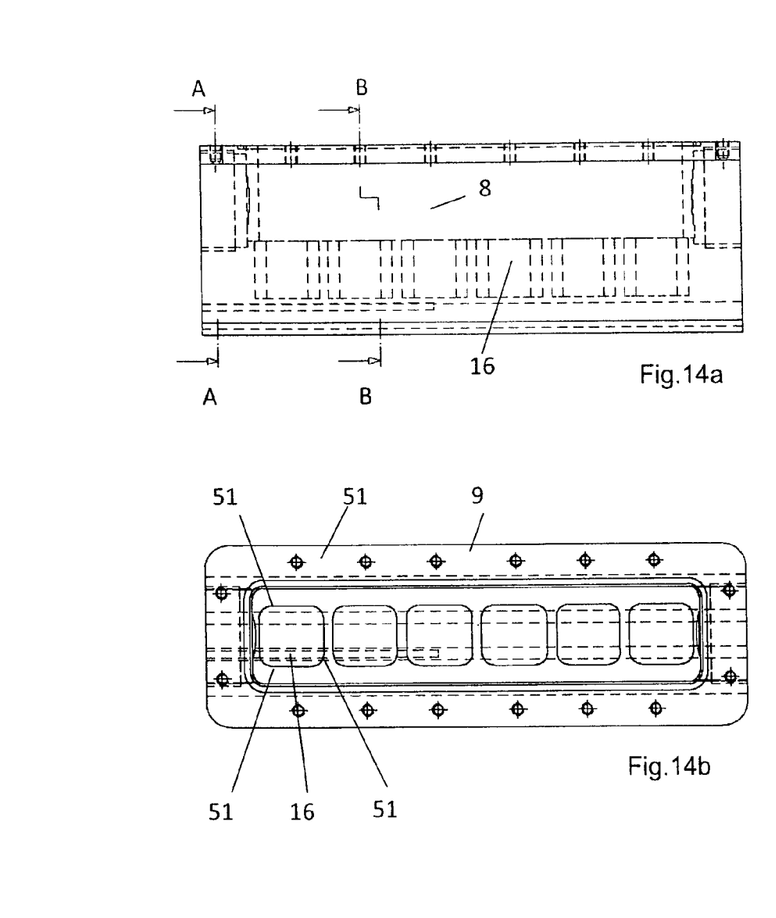
FIGS. 14a-14e are perspective and cross-section views of an evaporator body of the evaporator of FIG. 13, FIGS. 15a-15e are perspective, plan and cross-section views of a closing plate for securing a cover plate that is further shown in FIGS. 16a-16e.
Figures 14C, 14D, 14E:
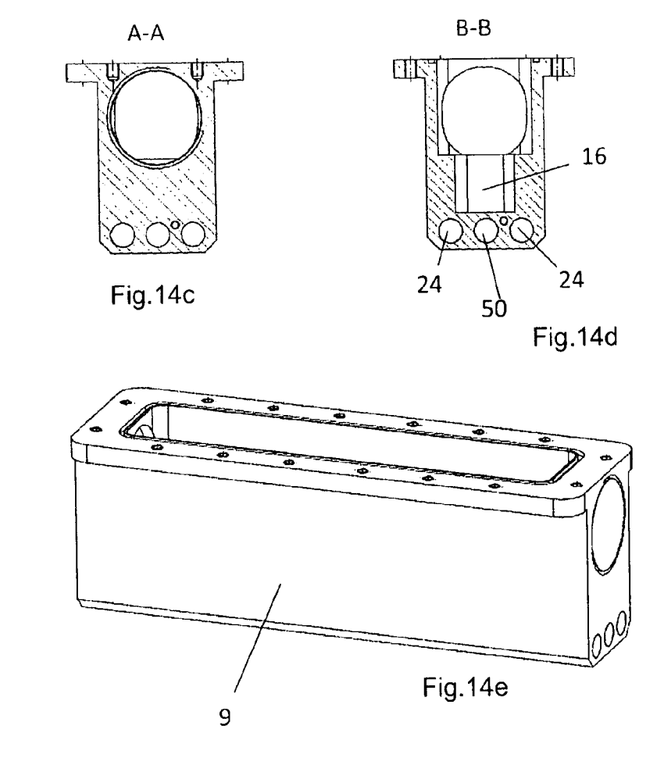

FIGS. 14a-14c are several different views of the evaporator body 9 of FIG. 13. A top view (FIG. 14b) shows blind holes 16 having a rectangular, in this case approximately square, contour, wherein a total of six blind holes are disposed in a row. The ratio between the blind hole length, the blind hole width and the blind hole depth is roughly 1:1:1. The blind hole length is 27.75 millimeters (mm), the blind hole width is 25 mm and the blind hole depth is 24 mm. As can be seen from FIG. 14b, the corners (edges 51) of the blind holes 16 are rounded in design. Each blind hole 16 is assigned a replaceable feed channel 28. The feed channels 28 project into the respective blind hole 16, thereby crossing the flow channel 8, so as to prevent an entrainment of liquid droplets.

FIGS. 15a-15e show the sealing cover 47. The sealing cover 47 includes a central feed 52, through which the decontamination liquid to be evaporated reaches the evaporator. As can be seen from FIG. 15d, the feed 52 is in the form of a hole with an internal thread, so that a corresponding flexible feed line (i.e., supply line) or an adapter for a flexible line of this kind can be secured to the feed 52.

Figure 15A:
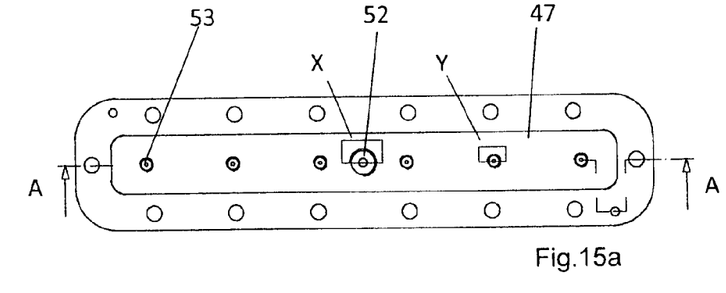
Figure 15B:
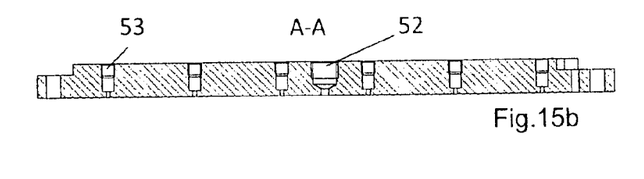
Figure 15C:
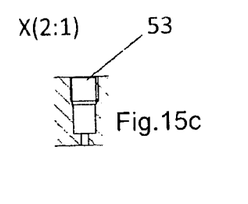
Figure 15D:
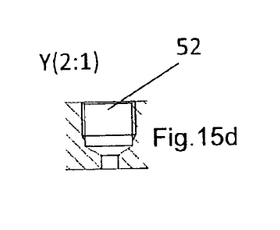
Figure 15E:
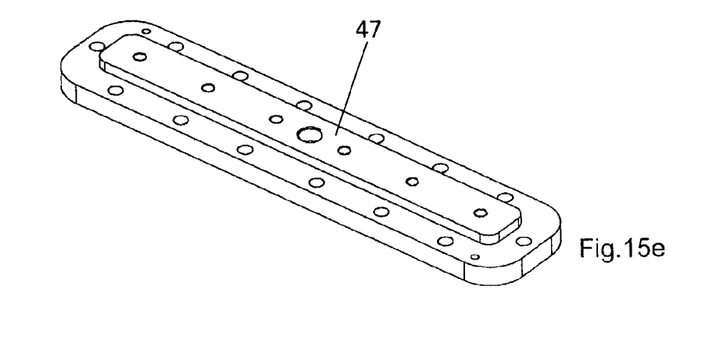
Figures 16A, 16B:
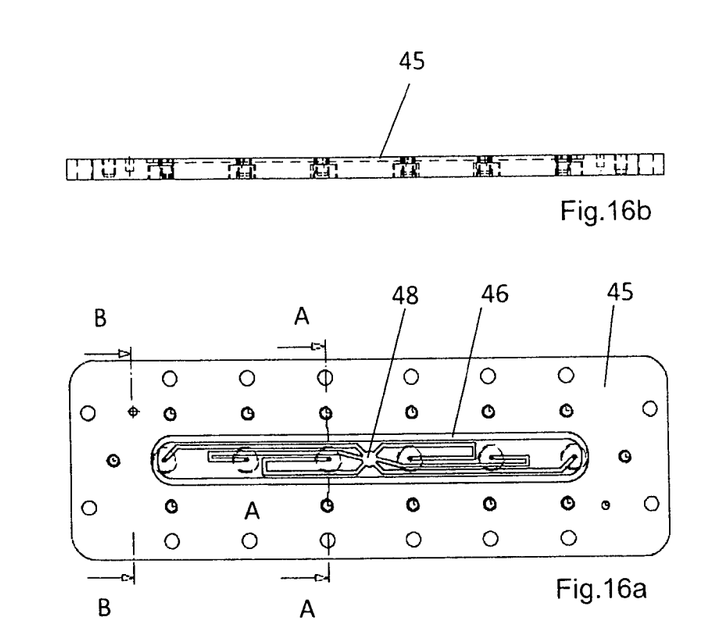
FIGS. 16a-16e are perspective, plan and cross-section views of a cover plate of the evaporator of FIG. 13 with supply channels of equal length introduced into the plate.
Figure 16C:
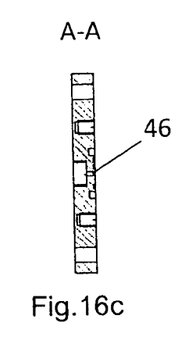
Figure 16D:
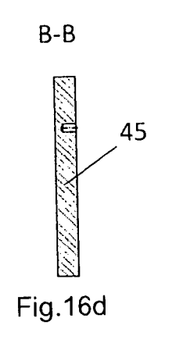
Figure 16E:
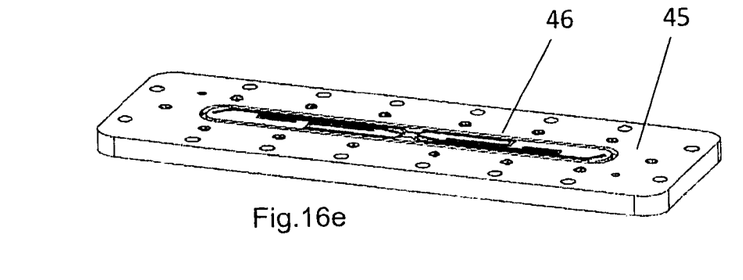

In addition, the sealing cover 47 includes six internally threaded holes 53 disposed in a row. Each of these threaded holes 53 may be assigned to an associated feed channel 28 (see FIG. 13). Each threaded hole 53 may further have a set screw (not shown) associated therewith to adjust the quantity of decontamination liquid being supplied. The set screw is not shown in the interests of clarity.

FIGS. 16a-16e show the cover plate 45 of FIG. 13, onto which the sealing plate 47 of FIGS. 15a-15e can be screwed, in order to seal the supply channels 46 inserted in the cover plate 45. All supply channels are the same length and have the same channel cross-section. The supply channels 46 emerge from a recess 48, which is disposed beneath the feed 52 in the assembled state. Decontamination liquid to be evaporated may flow from the recess, 48 via the supply channels 46, to the feed channels 28 (see FIG. 13). In order to achieve an equal length for the supply channels 46, they may be formed differently, in some cases with a change of direction. The supply channels 46 have a rectangular cross-section in the exemplary embodiment shown (see FIG. 16c). In the assembled state, the cover plate 45 seals the flow channel 8 for fresh air, for example compressed air or dried ambient air. The fresh air preferably has a relative humidity below 10%.

REFERENCE LIST

1 Device
2 First end
3 Connection
4 Second end
5 Lower device section
6 Internally threaded hole
7 Internally threaded hole
8 Flow channel
9 Evaporator body
10 Casing
11 Upper device section
12 Distributor chamber
13 Transport screw
14 Row
15 Row
16 Blind hole
17 Inlet opening
18 Blind hole base
19 Base end
20 Longitudinal side
21 Longitudinal side
22 Heating unit
23 Temperature sensor
24 Bore
25 Securing flange
26 Counter-flange
27 Connection
28 Feed channel
29 Luer-Lock connection piece
30 Adaptor
31 Set screw
32 Cylinder jacket surface
33 Assembly
34 Space to be decontaminated
35 Inlet connection
36 Outlet connection
37 Filter
38 Fresh air line
39 Temperature control mechanism
40 Line
41 Regulating line
42 Discharge line
43 Filter
44 Bypass line
45 Cover plate
46 Supply channels
47 Sealing plate
48 Recess
49 Heating rods
50 Opening
51 Edges
52 Feed
53 Internally threaded holes

The invention claimed is:

1. A device for generating decontamination agent vapor, comprising:
an evaporator body;
a heating unit for heating the evaporator body; and
a plurality of feed channels for feeding decontamination agent liquid to be evaporated to the evaporator body,
wherein a plurality of blind holes are provided in the evaporator body, the blind holes are each assigned at least one of the plurality of feed channels, and the feed channels are configured so that the decontamination agent liquid can be dropped directly into the blind holes.

2. The device according to claim 1, wherein a cross-sectional area of the blind holes is constant over a length of the blind holes.

3. The device according to claim 1, wherein a cross-sectional area of the blind holes has an at least approximately rectangular shape with rounded corners.

4. The device according to claim 1, wherein a cross-sectional surface of the blind holes diminishes at least one of continuously and in a stepped manner as a distance from an inlet of the blind holes increases.

5. The device according to claim 1, wherein the blind holes are spaced apart from one another.

6. The device according to claim 1, wherein the evaporator body is prismatic at least in sections, and has a length extension greater than a width extension.

7. The device according to claim 1, wherein the blind holes are disposed in at least one row extending in the direction of a longitudinal extension of the evaporator body.

8. The device according to claim 1, wherein the heating unit extends along at least one of:
two longitudinal sides of the evaporator body facing away from each other,
a lower base surface, and
an intermediate plane disposed between two rows of said blind holes.

9. The device according to claim 1, wherein the heating unit comprises at least one heating rod, said heating rod being contained in a longitudinal opening in the evaporator body.

10. The device according to claim 1, wherein the plurality of feed channels are configured to project into the plurality of blind holes.

11. The device according to claim 1, wherein the plurality of feed channels are interchangeable.

12. The device according to claim 1, wherein each of the feed channels are formed from injection needles having a Luer-Lok connection.

13. The device according to claim 1, further comprising a distributor chamber spaced apart from the evaporator via a flow channel, the flow channel configured to supply carrier air, wherein the distributor chamber is assigned to the feed channels.

14. The device according to claim 1, wherein a milled supply channel is assigned to each of said plurality of feed channels, the supply channels being the same length and having the same flow cross-section, the supply channels configured to be supplied by a common supply line.

15. The device according to claim 1, wherein a flow volume of each of the feed channels can be adjusted by a set screw.

16. An assembly comprising a space to be decontaminated, and a device for generating decontamination agent vapor according to claim 1.

17. An assembly according to claim 16, wherein the device is configured so that it can be supplied with fresh air as the carrier air from outside the space to be decontaminated.

18. An assembly according to claim 17, wherein the fresh air supply is compressed air or ambient air.

19. An assembly according to claim 16, wherein the device is connected to one of a bypass line to a fresh air line and an inlet from a fresh air line.

* * * * *